(12) United States Patent
Ray et al.

(10) Patent No.: US 12,023,489 B2
(45) Date of Patent: Jul. 2, 2024

(54) RESORBABLE IMPLANT FOR STIMULATING TISSUE, SYSTEMS INCLUDING SUCH IMPLANT, AND METHODS OF USING

(71) Applicants: Washington University, St. Louis, MO (US); Northwestern University, Evanston, IL (US)

(72) Inventors: Wilson Z. Ray, St. Louis, MO (US); Matthew R. MacEwan, St. Louis, MO (US); Zohny S. Zohny, St. Louis, MO (US); John A. Rogers, Evanston, IL (US)

(73) Assignees: Washington University, St. Louis, MO (US); Northwestern University, Evanston, IL (US)

( * ) Notice: Subject to any disclaimer, the term of this patent is extended or adjusted under 35 U.S.C. 154(b) by 274 days.

(21) Appl. No.: 17/507,291

(22) Filed: Oct. 21, 2021

(65) Prior Publication Data
US 2022/0040476 A1 Feb. 10, 2022

Related U.S. Application Data

(63) Continuation of application No. 16/608,218, filed as application No. PCT/US2018/029437 on Apr. 25, 2018, now Pat. No. 11,179,564.
(Continued)

(51) Int. Cl.
*A61N 1/20* (2006.01)
*A61N 1/04* (2006.01)
(Continued)

(52) U.S. Cl.
CPC ........... *A61N 1/205* (2013.01); *A61N 1/0456* (2013.01); *A61N 1/0504* (2013.01);
(Continued)

(58) Field of Classification Search
CPC ...... A61N 1/0456; A61N 1/05; A61N 1/0504; A61N 1/20; A61N 1/205; A61N 1/326; A61N 1/37217; A61N 1/375
See application file for complete search history.

(56) References Cited

U.S. PATENT DOCUMENTS

| | | |
|---|---|---|
| 4,883,057 A | 11/1989 | Broderick |
| 5,406,956 A | 4/1995 | Farwell |
| | (Continued) | |

FOREIGN PATENT DOCUMENTS

| | | |
|---|---|---|
| EP | 2381848 A1 | 11/2011 |
| WO | 2002000110 A1 | 1/2002 |
| | (Continued) | |

OTHER PUBLICATIONS

PCT International Search Report and Written Opinion, Application No. PCT/2018/029437, dated Aug. 2, 2018, 7 pps.
(Continued)

*Primary Examiner* — Brian T Gedeon
(74) *Attorney, Agent, or Firm* — Armstrong Teasdale LLP

(57) ABSTRACT

A system for stimulating tissue generally comprises a resorbable implant. The resorbable implant includes a substrate, at least one contact, and a transceiver, wherein the substrate, the at least one contact, and the transceiver are resorbable. The system also includes a controller configured to communicate with the transceiver of the resorbable implant and a power supply connected to the controller. The controller delivers power to the resorbable implant from the power supply. The resorbable implant delivers electrical stimulation to tissue when the resorbable implant receives power.

19 Claims, 17 Drawing Sheets

Related U.S. Application Data

(60) Provisional application No. 62/489,880, filed on Apr. 25, 2017.

(51) Int. Cl.
*A61N 1/05* (2006.01)
*A61N 1/372* (2006.01)
*A61N 1/375* (2006.01)

(52) U.S. Cl.
CPC ......... *A61N 1/37217* (2013.01); *A61N 1/375* (2013.01); *A61N 1/20* (2013.01)

(56) References Cited

U.S. PATENT DOCUMENTS

| | | | |
|---|---|---|---|
| 5,441,527 A | 8/1995 | Erickson et al. | |
| 5,699,808 A | 12/1997 | John | |
| 6,034,295 A | 3/2000 | Rehberg et al. | |
| 6,067,467 A | 5/2000 | John | |
| 6,120,502 A | 9/2000 | Michelson | |
| 6,195,576 B1 | 2/2001 | John | |
| 6,605,089 B1 | 8/2003 | Michelson | |
| 7,373,198 B2 | 5/2008 | Bibian et al. | |
| 7,431,734 B2 | 10/2008 | Danoff et al. | |
| 7,570,991 B2 | 8/2009 | Milgramm et al. | |
| 7,574,254 B2 | 8/2009 | Milgramm et al. | |
| 7,594,122 B2 | 9/2009 | Milgramm et al. | |
| 7,603,168 B2 | 10/2009 | Bibian et al. | |
| 7,676,263 B2 | 3/2010 | Harris et al. | |
| 7,869,884 B2 | 1/2011 | Scott et al. | |
| 8,071,949 B2 | 12/2011 | Majewski et al. | |
| 8,078,282 B2 | 12/2011 | Nycz | |
| 8,244,341 B2 | 8/2012 | Hinrikus et al. | |
| 8,290,596 B2 | 10/2012 | Wei et al. | |
| 8,298,078 B2 | 10/2012 | Sutton et al. | |
| 8,350,804 B1 | 1/2013 | Moll | |
| 8,380,314 B2 | 2/2013 | Panken et al. | |
| 8,380,319 B2 | 2/2013 | Berger | |
| 8,538,512 B1 | 9/2013 | Bibian et al. | |
| 8,560,100 B2 | 10/2013 | Sarkis et al. | |
| 8,600,493 B2 | 12/2013 | Tanner et al. | |
| 8,761,869 B2 | 6/2014 | Leuthardt et al. | |
| 8,798,735 B1 | 8/2014 | Bibian et al. | |
| 8,838,249 B2 | 9/2014 | Nycz | |
| 8,934,965 B2 | 1/2015 | Rogers et al. | |
| 8,938,289 B2 | 1/2015 | Einav et al. | |
| 9,072,482 B2 | 7/2015 | Sarkela et al. | |
| 9,162,064 B2 | 10/2015 | Faltys et al. | |
| 9,179,854 B2 | 11/2015 | Doidge et al. | |
| 2003/0064411 A1 | 4/2003 | Herath et al. | |
| 2006/0094974 A1 | 5/2006 | Cain | |
| 2006/0129324 A1 | 6/2006 | Rabinoff et al. | |
| 2006/0276870 A1 | 12/2006 | McGinnis | |
| 2006/0287660 A1 | 12/2006 | Syed et al. | |
| 2007/0213784 A1 | 9/2007 | Pless | |
| 2008/0183097 A1 | 7/2008 | Leyde et al. | |
| 2009/0048530 A1 | 2/2009 | Sarkela et al. | |
| 2009/0198145 A1 | 8/2009 | Chow | |
| 2009/0247860 A1 | 10/2009 | Djuric et al. | |
| 2010/0069775 A1 | 3/2010 | Milgramm et al. | |
| 2010/0125219 A1 | 5/2010 | Harris et al. | |
| 2010/0152811 A1 | 6/2010 | Flaherty | |
| 2010/0159486 A1 | 6/2010 | Liotta et al. | |
| 2010/0185268 A1 | 7/2010 | Fowler et al. | |
| 2010/0268057 A1 | 10/2010 | Firminger et al. | |
| 2010/0268108 A1 | 10/2010 | Firminger et al. | |
| 2010/0324440 A1 | 12/2010 | Moore et al. | |
| 2011/0166430 A1 | 7/2011 | Harris et al. | |
| 2013/0072292 A1 | 3/2013 | Sutton et al. | |
| 2013/0131755 A1 | 5/2013 | Panken et al. | |
| 2013/0150936 A1 | 6/2013 | Takahashi | |
| 2013/0177883 A1 | 7/2013 | Barnehama et al. | |
| 2013/0267866 A1 | 10/2013 | Nakashima et al. | |
| 2014/0051044 A1 | 2/2014 | Badower et al. | |
| 2014/0200626 A1 | 7/2014 | Campbell et al. | |
| 2014/0316230 A1 | 10/2014 | Denison et al. | |
| 2014/0364721 A1 | 12/2014 | Lee et al. | |
| 2014/0377758 A1 | 12/2014 | Dubnau et al. | |
| 2014/0378815 A1 | 12/2014 | Huang et al. | |
| 2015/0038869 A1 | 2/2015 | Simon et al. | |
| 2015/0073575 A1 | 3/2015 | Sarkis | |
| 2015/0080695 A1 | 3/2015 | Rogers et al. | |
| 2015/0094914 A1 | 4/2015 | Abreu | |
| 2015/0105687 A1 | 4/2015 | Abreu | |
| 2015/0141773 A1 | 5/2015 | Einav et al. | |
| 2015/0199010 A1 | 7/2015 | Coleman et al. | |
| 2015/0245156 A1 | 8/2015 | Tsang | |
| 2015/0258339 A1 | 9/2015 | Burchiel et al. | |
| 2015/0265201 A1 | 9/2015 | Arbas | |
| 2015/0272496 A1 | 10/2015 | Klappert et al. | |
| 2015/0297109 A1 | 10/2015 | Garten et al. | |
| 2015/0338917 A1 | 11/2015 | Steiner et al. | |

FOREIGN PATENT DOCUMENTS

| | | |
|---|---|---|
| WO | 2012145652 A1 | 10/2012 |
| WO | 2013149683 A1 | 10/2013 |
| WO | 2013159683 A1 | 10/2013 |
| WO | 2014137549 A1 | 9/2014 |
| WO | 2014172775 A1 | 10/2014 |
| WO | 2015047147 A1 | 4/2015 |
| WO | 2015130955 A1 | 9/2015 |
| WO | 2015160715 A1 | 10/2015 |
| WO | 2015161300 A1 | 10/2015 |
| WO | 2015164477 A1 | 10/2015 |

OTHER PUBLICATIONS

Gordon et al.: Strategies to promote peripheral nerve regeneration: electrical stimulation and/or exercise. Eur J Neurosci 43:336-350, 2016.

Gordon et al.: Brief electrical stimulation accelerates axon regeneration in the peripheral nervous system and promotes sensory axon regeneration in the central nervous system. Motor Control 13:412-441, 2009.

Hwang et al: 25th anniversary article: materials for high-performance biodegradable semiconductor devices. Adv Mater 26:1992-2000, 2014.

Kang et al: Stent Thrombosis With Drug-Eluting Stents and Bioresorbable Scaffolds: Evidence From a Network Meta-Analysis of 147 Trials. JACC Cardiovasc Interv 9:1203-1212, 2016.

Kang et al: Bioresorbable silicon electronic sensors for the brain. Nature 530:71-76, 2016.

Noble et al.: Analysis of upper and lower extremity peripheral nerve injuries in a population of patients with multiple injuries. J Trauma 45:116-122, 1998.

Willand et al.: Electrical Stimulation to Promote Peripheral Nerve Regeneration. Neurorehabil Neural Repair 30:490-496, 2016.

RESORBABLE IMPLANT FOR STIMULATING TISSUE, SYSTEMS INCLUDING SUCH IMPLANT, AND METHODS OF USING

CROSS-REFERENCE TO RELATED APPLICATION

This application is a continuation of U.S. patent application Ser. No. 16/608,218, filed Oct. 25, 2019, which is a U.S. National Phase Application of PCT/US2018/029437, filed Apr. 25, 2018, which claims priority to U.S. Provisional Patent Application Ser. No. 62/489,880, filed Apr. 25, 2017, the entire disclosures of which are hereby incorporated by reference in their entireties.

STATEMENT REGARDING FEDERALLY SPONSORED RESEARCH & DEVELOPMENT

This invention was made with government support under W31P4Q-15-C-0027 awarded by the Department of the Defense DARPA. The government has certain rights in the invention.

BACKGROUND

The present disclosure relates generally to tissue stimulating implants and tissue stimulation systems and, more particularly, to a resorbable implant for stimulating tissue, a tissue stimulation system including a resorbable implant, and a method of using a resorbable implant.

Some tissue injuries may be treated using surgical intervention and therapy. For example, surgical procedures may be performed to correct issues of the spine by fusing vertebrae along the spine or surgical procedures may be performed to treat intracranial lesions such as brain tumors and epileptic foci. However, the surgical procedures may require tissue growth and may be unsuccessful in treating the tissue injuries if tissue growth is insufficient. In addition, many target tissue locations are not surgically accessible using traditional procedures. As a result, options for some patients such as patients with surgically inaccessible lesions may be limited to medical therapy and radiotherapy. In addition, surgical procedures and therapies have not been completely successful in treating tissue injuries and patients may have motor and/or sensor dysfunction after treatment.

Tissue stimulation may promote tissue growth to help individuals recover from injuries and may otherwise improve patient health. For example, devices that emit pulses of low-level electrical current can be used to stimulate tissue and may be implanted into a patient during a procedure such as a spinal fusion procedure. In addition, such devices may be used to modify tissue function. The devices may be implanted directly at a treated site or subcutaneously. At least some known devices include electronics for delivering the pulses and a power supply for powering the electronics. The devices deliver electrical pulses to the tissue throughout a treatment period. Afterwards, the devices may be left inside the patient as a permanent implant. However, the permanent implant may require long-term management and increase the cost of treatment. In addition, the permanent implant could contribute to complications with the patient's health. Alternatively, the implant may be removed from the patient after the treatment has concluded or after the device has reached its service life. However, the patient has to undergo an additional procedure to remove the implant which exposes the patient to risks such as infection.

It is desirable, therefore, to provide a system for stimulating tissue growth that includes a completely resorbable implant.

BRIEF DESCRIPTION

In one aspect, a system for stimulating tissue includes a resorbable implant. The resorbable implant generally comprises a substrate, at least one contact, and a transceiver, wherein the substrate, the at least one contact, and the transceiver are resorbable. The system also includes a controller configured to communicate with the transceiver of the resorbable implant and a power supply connected to the controller. The controller delivers power to the resorbable implant from the power supply. The resorbable implant delivers electrical stimulation to the tissue when the resorbable implant receives power.

In another aspect, a method of stimulating tissue generally comprises positioning a resorbable implant at a treatment location within a body of an animal. The resorbable implant includes a substrate, at least one contact, and a transceiver, wherein the substrate, the at least one contact, and the transceiver are resorbable. The method further includes sending a signal to the transceiver from a controller positioned on an exterior of the body. The transceiver is supported by the substrate. The method also includes receiving power at the resorbable implant from a power supply connected to the controller and providing electrical stimulation to tissue at the treatment location through the at least one contact.

In yet another aspect, a resorbable implant for providing electrical pulses to stimulate tissue generally comprises a transceiver configured to receive signals from a controller and electronics configured to provide electrical pulses based on the signals received from the controller. The resorbable implant also includes a substrate supporting the transceiver and the electronics. The resorbable implant further includes contacts configured to be positioned on the tissue to deliver the electrical pulses to the tissue. The resorbable implant also includes leads extending between the substrate and the contacts. The contacts, substrate, electronics, leads, and transceiver are resorbable.

DETAILED DESCRIPTION

As used herein, the terms "resorbable" and "resorb" refer to assimilation of a material into an animal. The term "tissue" refers to a cellular structure performing a specific function in an animal. The term "animal" refers to a multicellular organism capable of voluntary movement. For example, animals include, without limitation, humans, horses, dogs, cats, mice, and rats. Thus, the implants, systems and methods disclosed herein are suitable for use in animals including, but not limited to, humans, horses, dogs, cats, mice, and rats.

Figure 1:
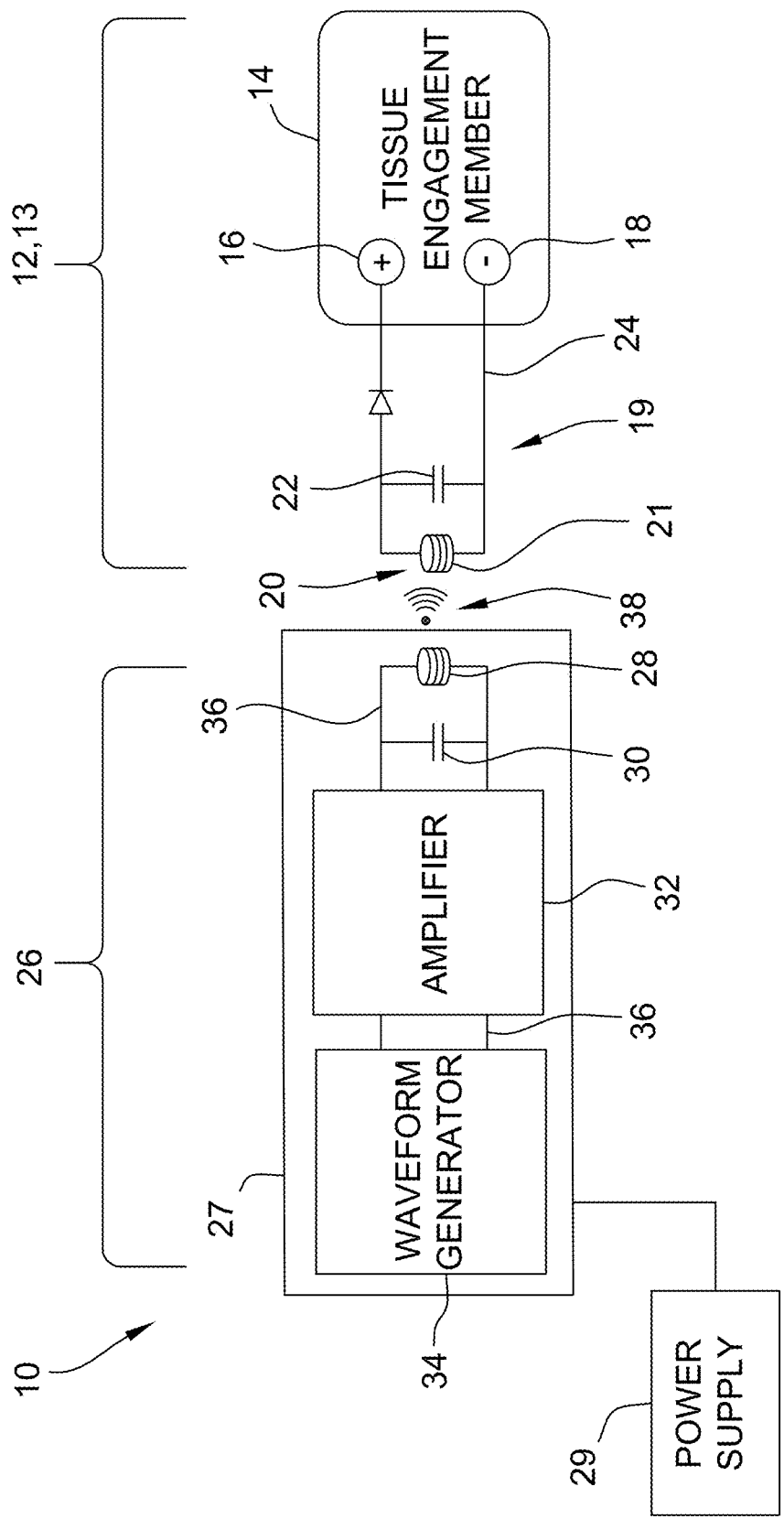
FIG. 1 is a schematic of a system for stimulating tissue including a resorbable implant.

Embodiments of a system for stimulating tissue growth include a resorbable implant. The system includes an external controller and the resorbable implant. The resorbable implant is an implantable medical device capable of delivering electrical stimulation to tissue. The external controller delivers wireless power and control signals to the resorbable implant to cause the resorbable implant to provide therapeutic electrical stimulation to targeted tissue within an animal. For example, the resorbable implant delivers electrical stimulation to bony tissue and thereby modulates bone formation in focal areas of an animal. In addition, the resorbable implant may deliver electrical stimulation to the central and peripheral nervous tissue. Moreover, the resorbable implant may deliver electrical stimulation to soft tissue to modify the function of the soft tissue. The resorbable implant may be completely resorbed by the animal FIG. 1 is a schematic view of a system 10 for stimulating tissue growth including a resorbable implant 12. The resorbable implant 12 is configured to be implanted within a body of an animal and includes materials that are fully resorbable by the animal. Accordingly, the resorbable implant 12 does not need to be removed after the service life of the resorbable implant 12 is over. The resorbable implant 12 includes a tissue engagement member 14 including a positive contact 16 and a negative contact 18. The resorbable implant 12 also includes a transceiver 20 and electronics 19 including a capacitor 22. At least one conductor 24 connects the transceiver 20, the capacitor 22, the positive contact 16, and the negative contact 18 to form a circuit. At least some of the electronics 19 such as the conductors 24 may be printed or laser-etched on a substrate 42 (shown in FIG. 2). For example, the conductors 24 may be traces formed by a conductive ink printed on the substrate 42.

The electronics 19 deliver electrical stimulation to a target (e.g., tissue of the animal being treated) via the contacts 16, 18 when power is supplied to the resorbable implant 12. In addition, the electronics 19 are configured to control amplitude and duration of the electrical stimulation provided to the targeted tissue. For example, the resorbable implant 12 may provide pulses having a duration of at least about 200 µs and a threshold voltage in a range of about 100 milli-Volts (mV) to about 300 mV. For example, the resorbable implant 12 may provide stable output currents across a range of input voltages, such as about 3 Volts (V) to about 2.5 V, and across a range of resistances, such as about 10 kilo Ohms (kΩ) to about 30 kΩ. The resorbable implant 12 may output a constant direct current (DC) electrical signal in a range of about 46 microamperes (uA) to about 51 uA. In other embodiments, the resorbable implant 12 may include any components and provide any electrical pulses that enable the system 10 to operate as described herein.

The transceiver 20 includes an antenna 21 that is configured to provide a magnetic field 46 for transmitting and/or receiving electrical signals 38 (shown in FIG. 1). The antenna 21 is a loop antenna having a bilayer, dual-coil configuration. The antenna 21 may be a metal such as magnesium. The antenna 21 may be approximately 50 µm thick. The transceiver 20 may further include a radiofrequency (RF) diode 23. The RF diode 23 includes a doped nanomembrane and electrodes. For example, in some embodiments, the doped nanomembrane may comprise silicon and may have a thickness of approximately 320 nanometers (nm). The electrodes may be a metal such as magnesium and may have a thickness of approximately 600 nm. The antenna 21 wirelessly couples to the transceiver 28 (shown in FIG. 1) and receives RF power from the transceiver 28. The transceivers 20, 28 may communicate using a frequency that reduces losses due to the biofluid and tissue between the transceivers 20, 28. For example, the transceivers 20, 28 may communicate using a frequency in a range of about 1 MHz to about 10 MHz. In some embodiments, the frequency may be approximately 5 MHz. The RF diode 23 and the capacitor 22 convert the RF power into a DC electrical current. In some embodiments, the electronics 19 provide at least 1 volt of electrical power. In other embodiments, the transceiver 20 may have other configurations without departing from some aspects of the disclosure.

The resorbable implant 12 is controlled by a controller 26 positioned exterior of the animal. In one suitable embodiment, the controller 26 includes a processor 27, a transceiver 28, a capacitor 30, an amplifier 32, and a waveform generator 34. At least one conductor 36 of the controller 26 connects the transceiver 28, the capacitor 30, the amplifier 32, and the waveform generator 34 to form a circuit. The waveform generator 34 generates electrical waveforms to provide a desired current through the conductor 36. The transceiver 28 transmits an electrical signal 38 based on the waveforms and the electrical signal 38 is received by the resorbable implant 12. Accordingly, the controller 26 and the resorbable implant 12 communicate wirelessly. The controller 26 is configured to control the resorbable implant 12 from the exterior of the body by transmitting the electrical signal 38 through at least a portion of the body. The resorbable implant 12 is configured to generate therapeutic electrical pulses based on the electrical signals 38 received from the controller 26. In other embodiments, the controller 26 and the resorbable implant 12 may communicate in any manner that enables the system 10 to operate as described herein.

In addition, the controller 26 may provide power to the resorbable implant 12 from a power supply 29. As a result, the resorbable implant 12 does not require an internal power supply which would hinder the resorption process. In addition, the size of the resorbable implant 12 may be reduced because the internal power supply is not required. In some embodiments, the capacitor 30 acts as a power storage component to temporarily store power provided by the controller 26. In other embodiments, the resorbable implant 12 may be powered in any manner that enables the resorbable implant 12 to function as described herein.

Figure 2:
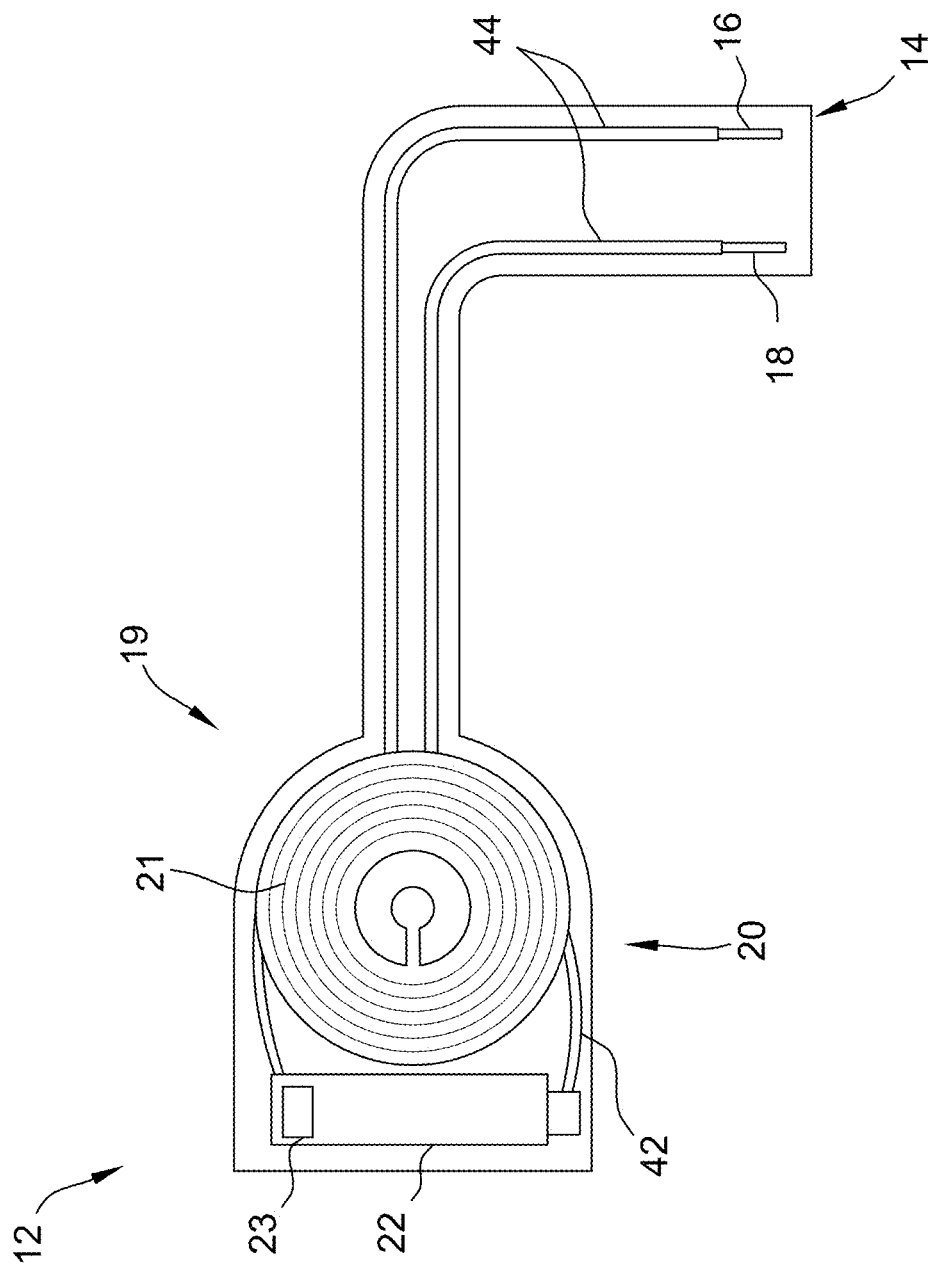
FIG. 2 is a top view of a suitable embodiment of a resorbable implant for use with the system shown in FIG. 1.

FIG. 2 is a top view of a suitable embodiment of the resorbable implant 12. The resorbable implant 12 includes the tissue engagement member 14, electronics 19, the transceiver 20, a substrate 42, and leads 44. The electronics 19 and the transceiver 20 are attached to and supported by the substrate 42. The leads 44 extend between and connect the electronics 19 and the contacts 16, 18. The leads 44 are flexible and enable the tissue engagement member 14 to be positioned relative to the substrate 42. In some embodiments, the electronics 19 include logical control circuits, demodulating circuits, pulse generators, charge storage components, and any other suitable electronic components. In other embodiments, the resorbable implant 12 may include any electronics 19 that enable the resorbable implant 12 to operate as described herein.

Figure 3:
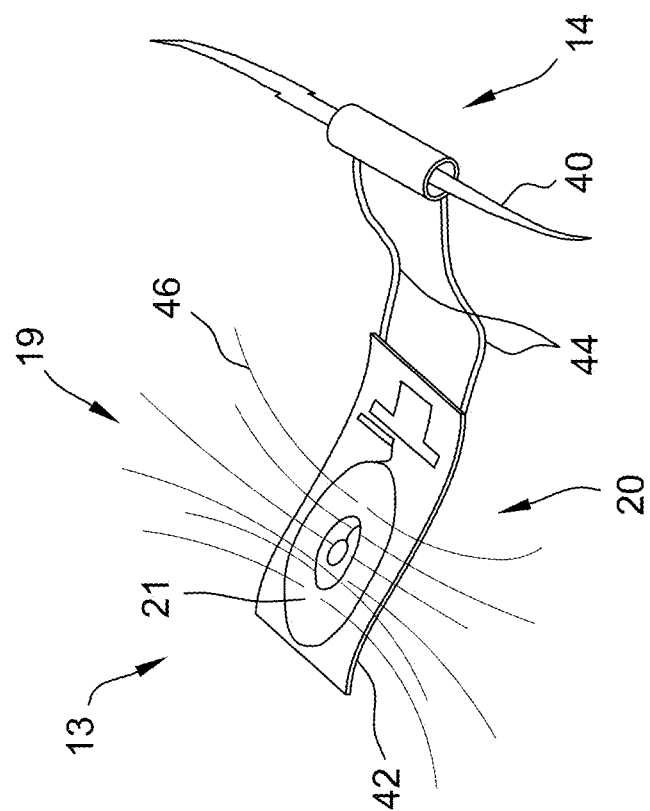
FIG. 3 is a perspective view of another suitable embodiment of the resorbable implant for use with the system shown in FIG. 1 positioned to deliver electric current to nervous tissue.

FIG. 3 is a perspective view of another suitable embodiment of the resorbable implant 12 positioned to deliver electrical pulses to tissue. In the illustrated embodiment, the resorbable implant 13 delivers therapeutic electrical pulses to targeted nervous tissue 40 within the body. In other embodiments, the system 10 may be configured for stimulating any tissue. For example, in some embodiments, the system 10 may deliver electrical pulses to boney tissue such as boney tissue 112 (shown in FIG. 9). In further embodiments, the system 10 may deliver electrical pulses to soft tissue including, without limitation, muscles, tendons, ligaments, fascia, nerves, fibrous tissues, fat, blood vessels, and synovial membranes. Accordingly, the system 10 may be used for treatment of, for example and without limitation, tissue dysfunction, long bone fractures, cases of long bone revision and non-union, spinal fusion, reconstructive surgery, cranial fixation, spinal instrumentation and stabilization, implantation of artificial joints and metallic prostheses, limb lengthening, tumor excision, osteoporosis, soft tissue damage and injuries, damaged cartilage, peripheral nervous tissue issues related to pain, sensation, and function, and tissue wounds or incisions resulting from trauma and surgery. In some embodiments, the system 10 may be used for modification of tissue function. For example, the resorbable implant 12, 13 may be implanted within a patient to provide short-term pain modulation such as for post-operative care.

The resorbable implant 13 may be used to deliver electrical stimulation to the targeted nervous tissue 40 according to a treatment plan. For example, the treatment plan may include delivering specified electrical pulses at regular intervals such as daily. In some embodiments, the resorbable implant 13 provides 20 hertz (Hz) of electrical stimulation to the nervous tissue 40 for approximately 1 hour during each treatment interval. The controller 26 (shown in FIG. 1) may be configured to automatically control the resorbable implant 13 according to the treatment plan. In further embodiments, the resorbable implant 13 is at least partially controlled based on user inputs.

Figure 4:
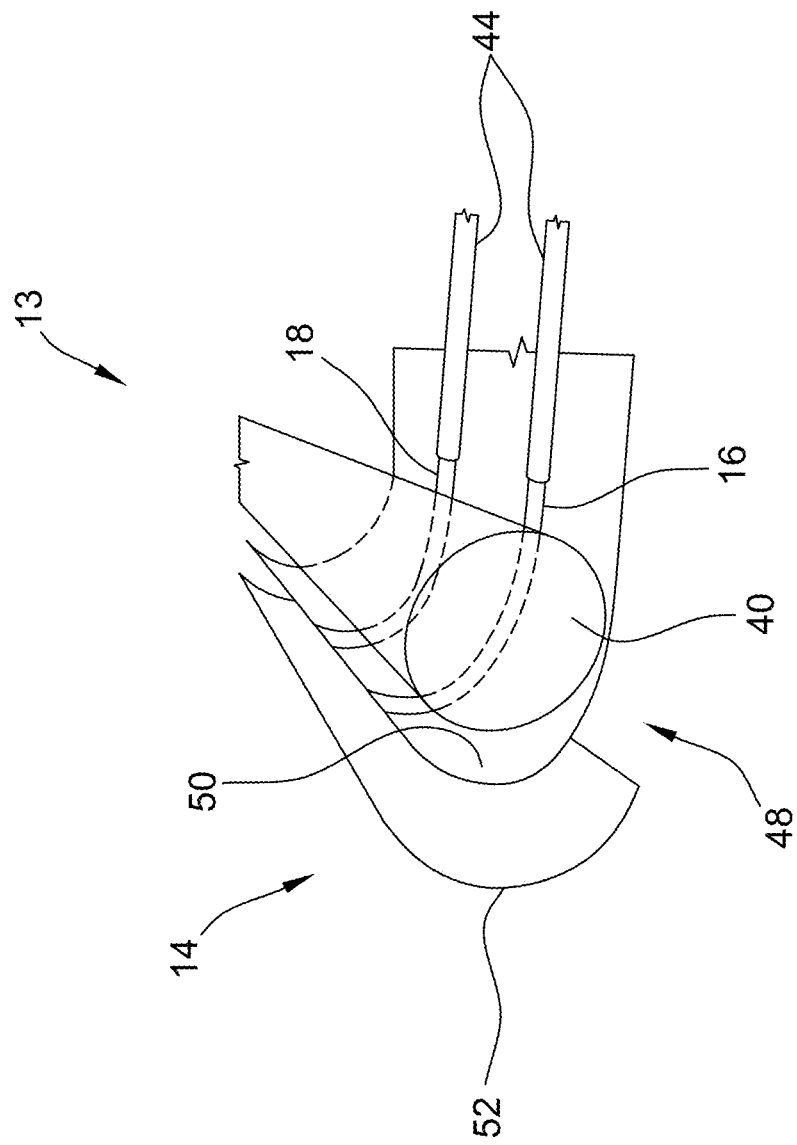
FIG. 4 is an enlarged perspective view of a tissue engagement member of the resorbable implant shown in FIG. 3 positioned on nervous tissue.

FIG. 4 is a perspective view of the tissue engagement member 14 of the resorbable implant 13 positioned on the nervous tissue 40. The tissue engagement member 14 is configured to be positioned on the nervous tissue 40 and deliver electrical pulses to the nervous tissue 40. For example, in the illustrated embodiment, the tissue engagement member 14 is a flexible cuff that wraps at least partially around the nervous tissue 40. In some embodiments, the tissue engagement member 14 may be a tube with a slit along the length of one side to facilitate positioning the tissue engagement member 14 on the nervous tissue 40. Accordingly, the tissue engagement member 14 reduces stresses on the nervous tissue 40. Sutures and/or staples may be used to secure the tissue engagement member 14. The contacts 16, 18 contact the nervous tissue 40 when the tissue engagement member 14 is positioned on the nervous tissue 40. The tissue engagement member 14 may include a flexible substrate 48 to support the contacts 16, 18. The flexible substrate 48 includes a nerve contact layer 50 and an outer layer 52. The contacts 16, 18 comprise a biodegradable metal strip embedded in the nerve contact layer 50 of the tissue engagement member 14. In other embodiments, the resorbable implants 12, 13 may include any tissue engagement member 14 that enables the resorbable implants 12, 13 to function as described herein.

With reference to FIGS. 2-4, the resorbable implants 12, 13 may include materials that are resorbable when implanted within an animal. Specifically, the tissue engagement member 14, the electronics 19, the substrate 42, and the leads 44 are all constructed of resorbable materials. Accordingly, the resorbable implants 12, 13 are completely resorbable when implanted within the animal. Specifically, the resorbable implants 12, 13 will be broken down by biofluids and be completely assimilated into the animal. After each resorbable implant 12, 13 is completely resorbed, the resorbable implant 12, 13 will be histologically undetectable. In addition, the resorbable implants 12, 13 are free of any materials that would be toxic to the body or cause cutaneous irritation at the implant site. As a result, the resorbable implants 12, 13 do not need to be removed after therapeutic treatment is completed and/or after the service life of the respective resorbable implant 12, 13 is reached. In addition, each resorbable implants 12, 13 will not remain as a permanent implanted medical device within the body.

Figure 26:
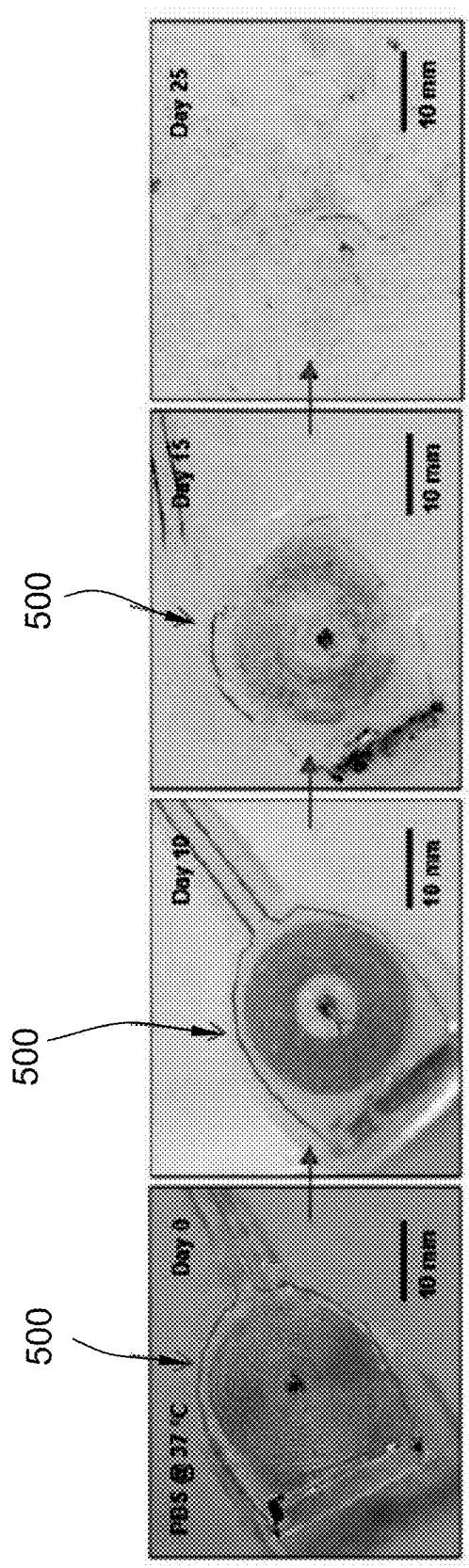
FIG. 26 is a series of time lapse photos of a resorbable implant dissolving due to immersion in phosphate buffer solution.

The thickness and/or types of materials used in the resorbable implants 12, 13 may be selected to provide a controlled resorption of the respective resorbable implant 12, 13 after a desired service life when exposed to biofluids found in and around subcutaneous tissue. For example, the resorbable implants 12, 13 may be constructed such that constituent materials completely dissolve within three weeks and all remaining residues completely resorb into the body after 25 days. For example, the resorbable implants 12, 13 may include P-type silicon nanomembranes (Si NMs) having a Boron content of about $10^{18}$ cm$^{-3}$ to $10^{20}$ cm$^{-3}$, Magnesium (Mg) foil, and/or N-type Si NMs having a Phosphorous content of about $10^{18}$ cm$^{-3}$ to $10^{20}$ cm$^{-3}$. In artificial cerebrospinal fluid (ACSF), P-type Si NMs dissolve at a rate of 23 nm/day and Mg foil dissolves at a rate of 4 μm/day. In phosphate buffer solution (PBS) at physiological temperature (approximately 37° C.), P-type Si NMs dissolves at a rate of 1.5 nm/day, N-type Si NMs dissolves at a rate of 2.95 nm/day, and Mg foils dissolves at a rate in a range of about 5 nm/day to about 10 nm/day. For example, FIG. 26 shows a series of time lapse photos of a resorbable implant 500 dissolving due to immersion in phosphate buffer solution having a pH of 7.4 and a temperature of 37° Celsius. Specifically, the photos are taken after the resorbable implant has been immersed for 10 days, 15 days, and 25 days. After 25 days, the resorbable implant 500 had been substantially dissolved. In alternative embodiments, the resorbable implants 12, 13 may be made of materials that dissolve at different rates without departing from some aspects of the disclosure.

In some embodiments, the resorbable implants 12, 13 are encapsulated in a material that controls the resorption of the materials in the resorbable implants 12, 13. For example, the resorbable implants 12, 13 may be encapsulated in a film or wax that is impermeable by fluids for a time. The encapsulation may naturally degrade and allow fluids to contact the resorbable material after a desired service life of the resorbable implants 12, 13. The thickness and type of material may be selected based on the desired service life of the resorbable implant 12, 13. For example, a polylactic-co-gylcolic acid encapsulation may allow fluid penetration to the resorbable materials within 10 hours and may completely dissolve within 20 days. A naturally degrading candelilla wax having a thickness of approximately 300 μm on each side of the resorbable implant 12, 13 may prevent resorption of the resorbable implant 12, 13 for at least ten days during immersion in PBS at a temperature of 37° C. and a pH 7.4. In the example, the encapsulation completely encloses the entire resorbable implant 12 and prevents fluid penetration during the service life of the resorbable implant 12. In alternative embodiments, at least some components of the resorbable implants 12, 13 may be at least partially resistant to resorption and may not require encapsulation.

In addition, the tissue engagement member 14 and conductive components of the resorbable implant 12, 13 may be constructed to account for accelerated bioresorption of exposed electrodes because of electrochemical effects from active electrical stimulation. Accordingly, the materials and configuration of the resorbable implant 12, 13 may be selected based on the desired treatment plan and the estimated amount of electrical stimulation provided by the resorbable implant 12, 13. For example, Mg wire and/or molybdenum (Mo) wire may be included in the resorbable implant 12, 13 and have been demonstrated to be stable for more than 300 min of continuous stimulation at an applied potential of 500 mV in PBS solution. In addition, the Mg wire and Mo wire have been demonstrated to be stable for 6 days under desired, pulsed electrical stimulation (200 μs, 100–300 mV, 1 h/d). Moreover, the tissue engagement member 14 may be constructed in a manner that provides increased stability.

Figure 5:
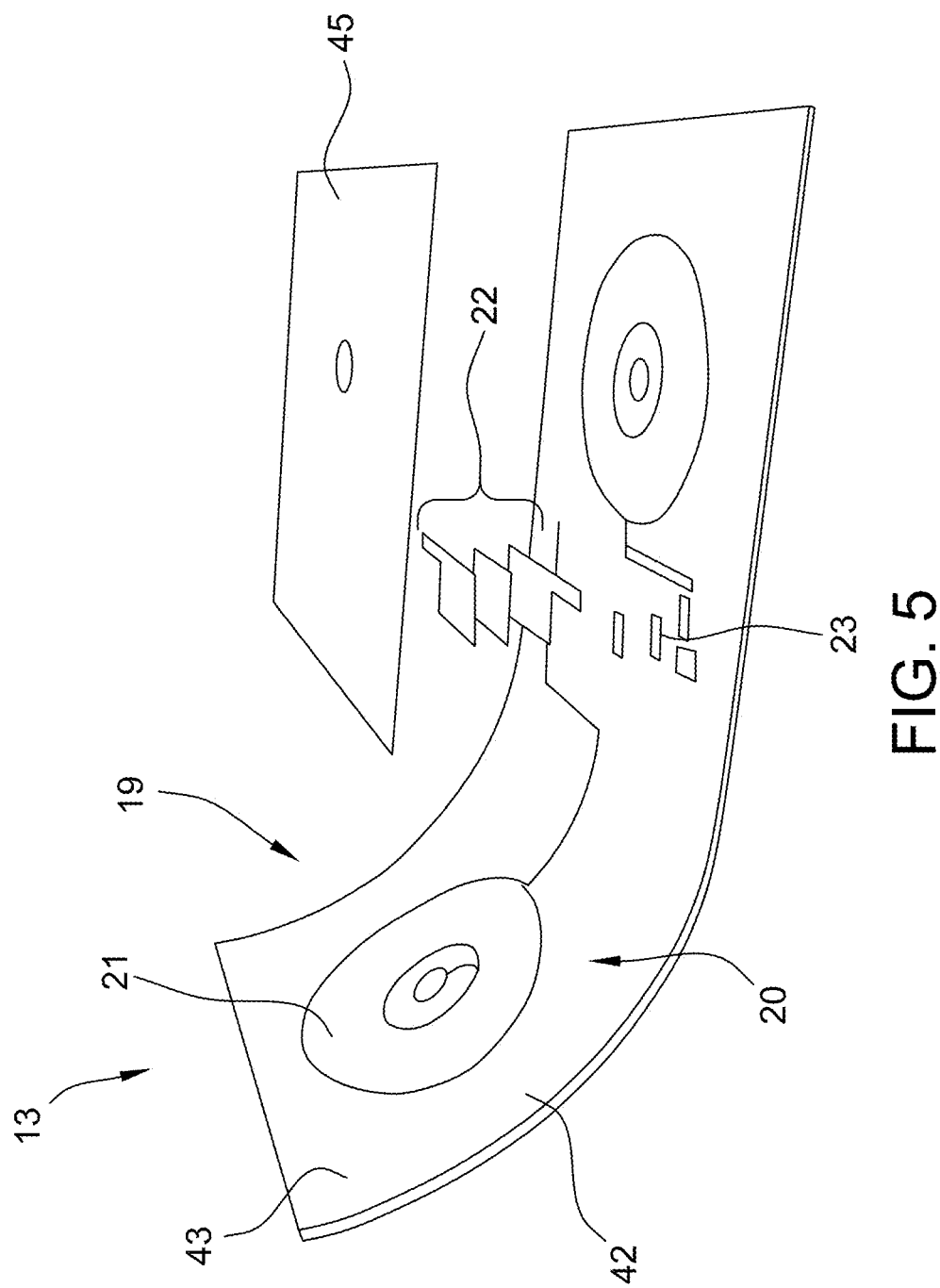
FIG. 5 is a partially exploded view of a portion of the resorbable implant shown in FIG. 3.

FIG. 5 is a partially exploded view of a portion of the resorbable implant 13 including the electronics 19. The substrate 42 includes multiple layers 43 that support the electronics 19. The substrate 42 may encapsulate at least a portion of the electronics 19. A dielectric layer 45 may be positioned between the layers 43. The layers 43 and/or the layer 45 may be constructed from a flexible material such as a polylactic-co-gylcolic acid (PLGA) polymer. In the illustrated embodiment, at least some of the layers are formed by a sheet of PLGA polymer that is folded over. The PLGA polymer is biodegradable and biocompatible which allows the substrate 42 to be implanted within the body of an animal and be resorbed by the animal. The components of the resorbable implant 13 may have thicknesses that are selected to allow the resorbable implant 13 to be resorbed after treatment is completed and to enable the resorbable implant 13 to be resorbed within a desired timeframe. For example, each layer 43, 45 of the substrate 42 may have a thickness in a range of about 1 μm to about 100 μm. In the illustrated embodiment, the thickness of each layer 43, 45 is about 50 μm. In other embodiments, the resorbable implant 13 may include any materials having any thickness that enable the resorbable implant 13 to operate as described herein. For example, in some embodiments, the substrate 42 may include materials such as, without limitation, polymers and candelilla wax.

Figure 6:
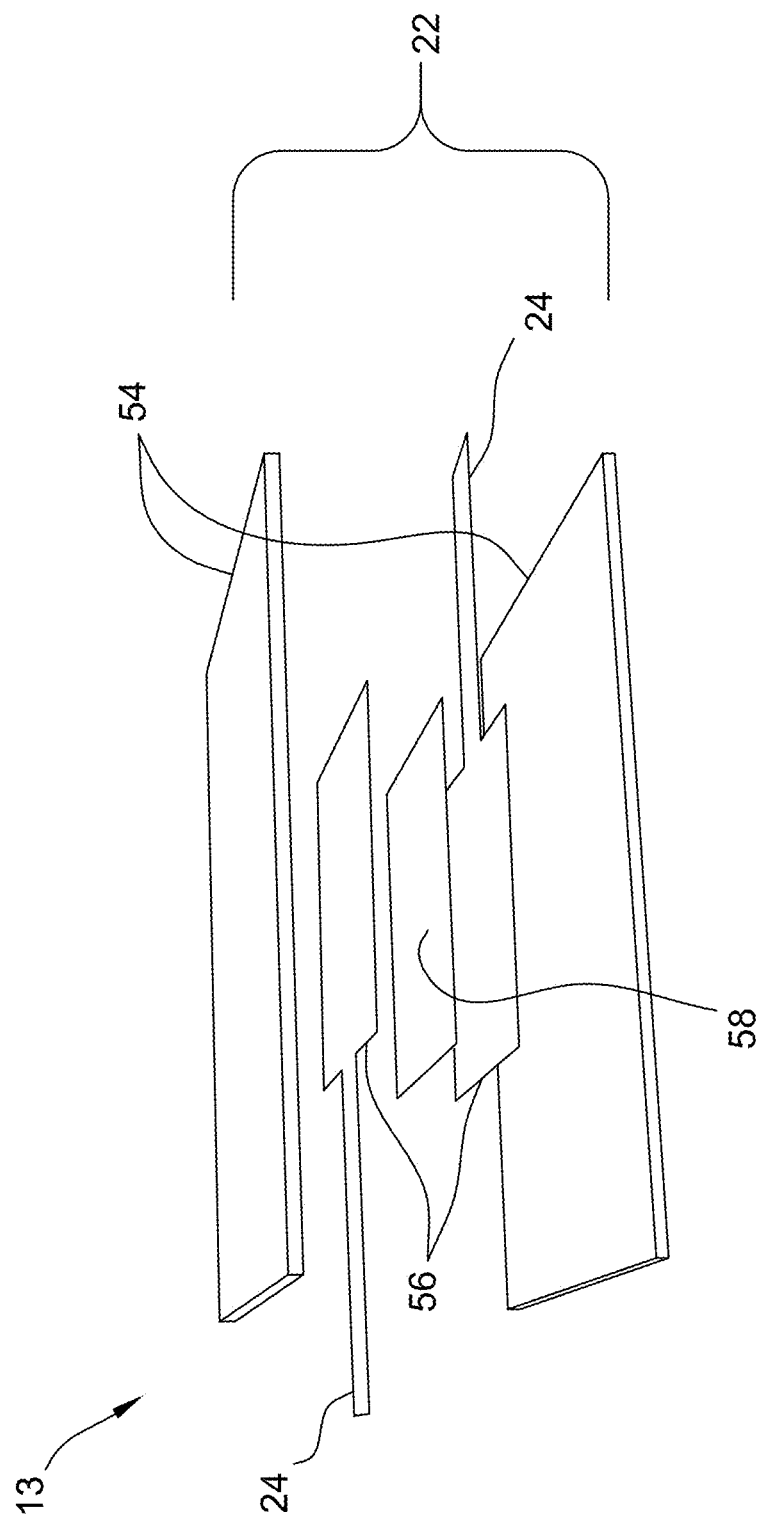
FIG. 6 is an exploded view of a capacitor of the resorbable implant shown in FIGS. 3-5.

FIG. 6 is an exploded view of a portion of the resorbable implant 13 including the capacitor 22. The capacitor 22 includes substrate layers 54, conductive layers 56, and an insulator 58. In the illustrated embodiment, the capacitor 22 has a stacked configuration and is a parallel plate capacitor. Specifically, the conductive layers 56 are positioned between the substrate layers 54. The insulator 58 is positioned between the conductive layers 56. The conductive layers 56 are coupled to conductors 24 that extend outward from the capacitor 22 on opposite sides. The substrate layers 54, conductive layers 56, and insulator 58 may be constructed of any materials that enable the resorbable implant 13 to operate as described herein. For example, the substrate layers 54 may be a PLGA polymer sheet. The conductive layers 56 may be a foil of metallic material such as magnesium. In some embodiments, the conductive layers 56 may have a thickness of approximately 50 micrometers (μm). The insulator 58 may comprise a sheet of silicon nitride that acts as a dielectric. The insulator 58 may have a thickness of approximately 600 nm. In other embodiments, the resorbable implant 13 may include any capacitor 22 that enables the resorbable implant 13 to operate as described herein.

With reference to FIGS. 1-6, a method of stimulating tissue growth includes positioning the resorbable implant 12 at a treatment location within a body. The resorbable implant 12 may be positioned during a surgical procedure. The tissue engagement member 14 may be secured on the tissue 40 and a portion of the resorbable implant 12 such as the substrate 42 and electronics 19 may be positioned a distance from the tissue 40. Any incisions in the body may be closed and repaired with the resorbable implant 12 implanted within the body. Accordingly, the system 10 allows for stimulation after the surgical procedure is completed. In contrast to some systems, the treatment is not limited to only during the surgical procedure. In addition, a surgical procedure is not required to remove the resorbable implant 12. Therefore, the system 10 reduces the number of surgical procedures required for the patient receiving tissue stimulation.

During a treatment interval, the controller 26 sends the electrical signal 38 to the resorbable implant 12 and the resorbable implant 12 receives power from the controller 26. When the resorbable implant 12 is powered, the resorbable implant 12 provides an electrical pulse to the tissue 40. The controller 26 may send electrical signals 38 to the resorbable implant 12 such that the resorbable implant 12 provides electrical pulses having a specified pulse duration continuous during a treatment interval. The controller 26 may repeat the treatment intervals according to a treatment plan until the end of the treatment plan or the end of the service life of the resorbable implant 12. After completion of the treatment plan and/or the end of the service life of the resorbable implant 12, the resorbable implant 12 is resorbed into the animal. In some embodiments, the resorbable implant 12 may have a service life that lasts any number of days, weeks, months, or years based on the intended application of the resorbable implant 12 and the desired treatment plan. Suitably, the service life of the resorbable implant 12 is greater than the duration of the intended treatment plan and the resorbable implant 12 will not be resorbed until after the treatment plan is completed.

Figure 7:
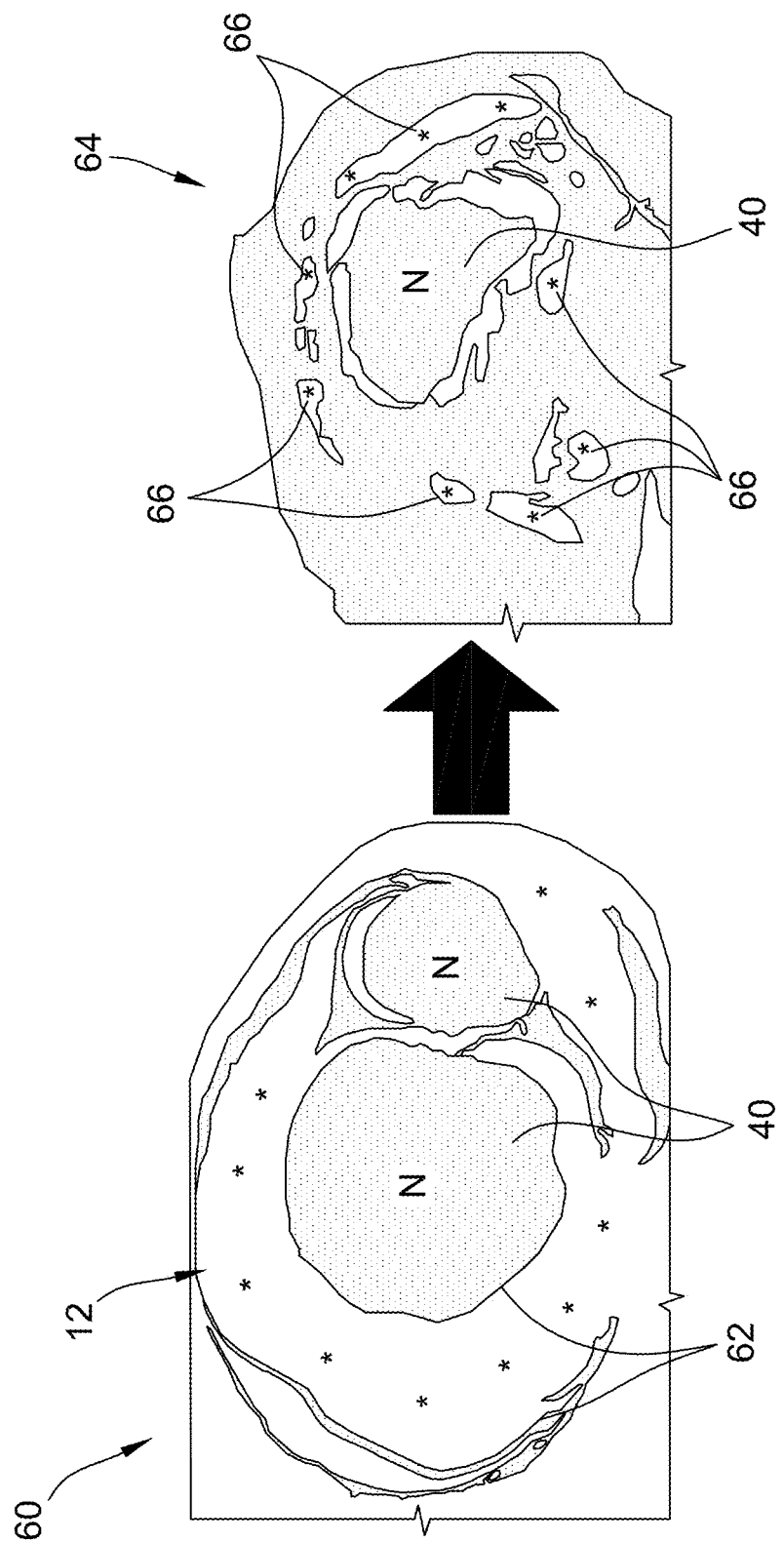
FIG. 7 is a series of images illustrating resorption of a resorbable implant into an animal.

FIG. 7 is a series of images illustrating resorption of the resorbable implant 12 into an animal. Image 60 shows at least a portion of the resorbable implant 12 positioned on nervous tissue 40 one month after implantation. The resorbable implant 12 and portions of the animal such as the nervous tissue 40 are clearly delineated along substantially continuous boundaries 62 of the resorbable implant 12. Image 64 shows the nervous tissue 40 and the resorbable implant 12 two months after implantation. After two months, the resorbable implant 12 has been at least partially resorbed into the animal. Accordingly, at least some components of the resorbable implant 12 have been broken down into fragments or particles 66 and/or assimilated into the animal. In particular, the nervous tissue 40 extends through and breaks up the boundaries 62 of the resorbable implant 12. Accordingly, the fragments 66 of the resorbable implant 12 are surrounded by the nervous tissue 40. In addition, at least some components of the resorbable implant 12 are no longer present and the resorbable implant 12 may not be functional after the resorbable implant 12 is at least partially resorbed. For example, at least some portions of the resorbable implant 12 are replaced by infiltrating macrophages, monocytes, lymphocytes, and fibroblasts consistent with prior reports of the foreign body response to PLGA materials. Metallic elements on the resorbable implant 12 have also undergone dissolution and bioresorption. At least some of the metallic traces dissolve into particulates that are phagocytized by local macrophages.

Accordingly, the resorbable implant 12 may be configured such that resorption of the resorbable implant 12 occurs after treatment is completed and/or after the service life of the resorbable implant ends. For example, if the desired treatment duration is two months, the resorbable implant 12 may be configured to remain functional for at least two months and to be substantially resorbed within three months.

The materials and thicknesses of the resorbable implant 12 may be adjusted to provide the desired service life and the resorption periods. In other embodiments, resorption of the resorbable implant 12 may be longer or shorter based on the placement of the resorbable implant 12 and/or the desired treatment to be delivered by the resorbable implant 12. In some embodiments, the resorbable implant 12 may be configured to remain functional for and/or be resorbed within any number of days, weeks, months, or years based on the intended application of the resorbable implant 12.

In addition, the resorbable implant 12 is compatible with the biomaterials. For example, image 64 does not show any focal or local cytotoxicity and necrosis or any additive inflammatory effect of the resorbable implant 12. Also, image 64 does not show any significant fibrotic response or formation of local scar tissue. Accordingly, the resorbable implant 12 may be compatible with and suitable for use with tissue such as peripheral nerve tissue which is particularly susceptible to post-operative adhesions, fibrosis, and compression in and around operative sites.

Figure 8:
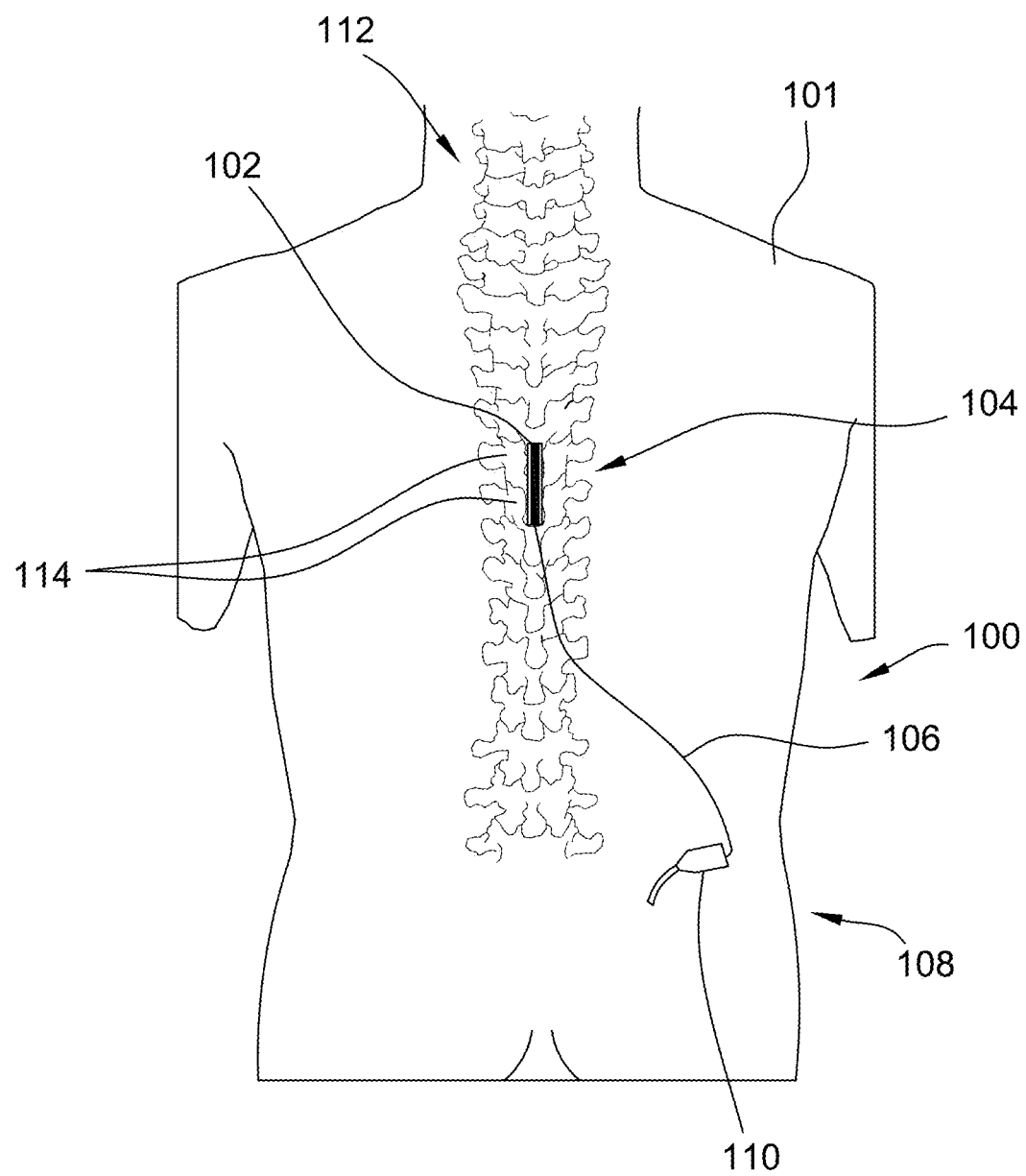
FIG. 8 is an illustration of a resorbable implant configured for stimulating tissue in a human body.

FIG. 8 is an illustration of a resorbable implant 100 configured for stimulating tissue growth within a human body 101. Resorbable implant 100 includes at least one contact 102, a lead 104, an extension wire 106, and electronics 108. The electronics 108 include a pulse generator 110 that delivers electrical pulses to a target via the contact 102 when power is supplied to the resorbable implant 100. The electronics 108 are configured to control amplitude and duration of the electrical stimulation provided to the targeted tissue. In some embodiments, the electronics 108 may include, for example and without limitation, a transceiver and a power storage unit. The extension wire 106 and the lead 104 connect the contact 102 to the pulse generator 110.

The resorbable implant 100 provides therapeutic pulses to the targeted tissue according to a treatment plan. The resorbable implant 100 may deliver anodic and/or cathodic DC electrical stimulation to the targeted tissue. For example, the resorbable implant 100 may provide cathodic DC current to induce local bone formation and/or anodic DC electrical stimulation to induce local bone resorption. In some embodiments, the contact 102 is positioned on the targeted tissue and is connected to a cathode (negative) of the electronics 108. A second contact 102 may be positioned on another portion of the human body 101 and be connected to an anode (positive) of the electronics 108. In such a configuration, the targeted tissue receives cathodic DC electrical stimulation from the resorbable implant. In other embodiments, the resorbable implant 100 may be configured to deliver any suitable current to the tissue.

In addition, the resorbable implant 100 is completely resorbable and does not require removal after the treatment plan is completed or after the resorbable implant 100 has reached its service life. In addition, the resorbable implant 100 does not require a permanent implantable power supply. As a result, the resorbable implant 100 reduces the cost of treatment and reduces health risks associated with the treatment. Moreover, the resorbable implant 100 does not require long-term management or care because the resorbable implant 100 will be completely assimilated into the human body 101 after treatment is concluded.

In the illustrated embodiment, the contact 102 is positioned on boney tissue 112, specifically along a spinal cord, of the body 101. The resorbable implant 100 is capable of inducing and/or accelerating bone formation in various anatomical locations without the need for pharmaceutical or biologic adjuncts. Accordingly, the resorbable implant 100 may stimulate tissue growth and enable union of vertebrae 114 of the spinal cord. The electronics 108 may be positioned a distance from the contact 102 at a surgically convenient location within the body 101. In other embodiments, the resorbable implant 100 may be positioned to deliver electrical pulses to any tissue of the body 101. For example, the resorbable implant 100 may be used for treatment of, without limitation, long bone fractures, cases of long bone revision and non-union, spinal fusion, reconstructive surgery, cranial fixation, spinal instrumentation and stabilization, implantation of artificial joints and metallic prostheses, limb lengthening, tumor excision, osteoporosis, and soft tissue.

Example 1

Tests were conducted to evaluate the effectiveness of resorbable implants. Operations were performed on test subjects, specifically rats, to create femoral defects in the test subjects. Specifically, a non-critical gap injury was formed in a femur of each rat. The test subjects were randomly divided into three groups. Permanent electrodes were implanted inside the bodies and attached to the femurs of the rats of group 2. Resorbable electrodes were implanted inside the bodies and attached to the femurs of the rats of group 3. The subjects in group 1 did not receive any stimulation. The subjects in group 2 received daily continuous stimulation at the femoral defect using the implanted permanent electrodes. The subjects in group 3 received daily continuous stimulation at the femoral defect using implanted resorbable electrodes. The subjects in groups 2 and 3 received 50 uA of DC electrical stimulation. After a two week period, the bones including the defects were harvested from the subjects and then evaluated. Qualitative and quantitative analysis for regional bone formation was performed using morphometric and density parameters. The bone formation was assessed using high resolution micro-computed tomography (micro-CT).

Figure 9:
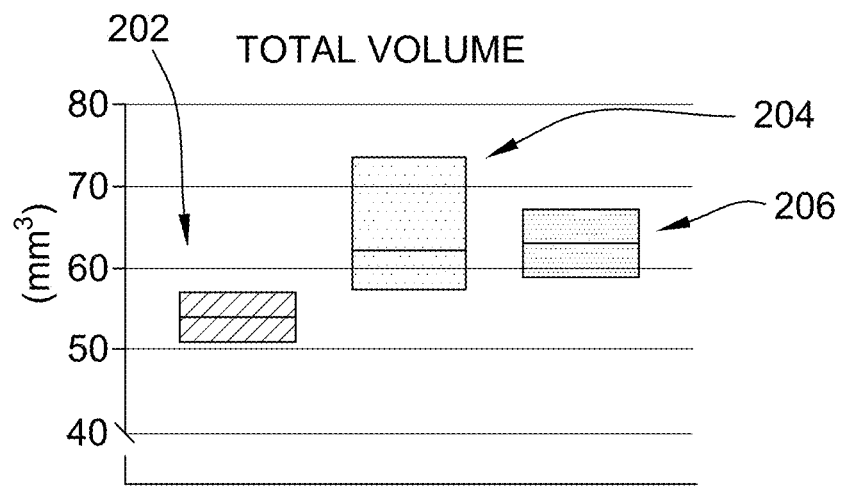
FIG. 9 is a graph comparing total volumes of tissue growth in test subjects after a two-week period.
Figure 10:
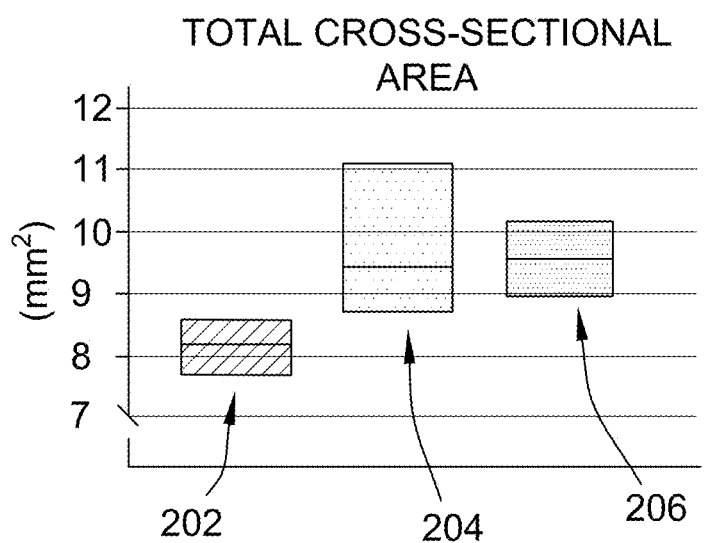
FIG. 10 is a graph comparing cross-sectional area of tissue in test subjects after a two-week period.

FIG. 9 is a graph comparing total volumes of boney tissue growth after a two-week period for the three groups. FIG. 10 is a graph comparing cross-sectional area of boney tissue after a two-week period for the three groups. In each graph, bar 202 represents group 1, bar 204 represents group 2, and bar 206 represents group 3. Total volume is measured in cubic millimeters on a scale from 40 mm$^3$ to 80 mm$^3$. Cross-sectional area is measured in square millimeters on a scale from 7 mm$^2$ to 12 mm$^2$. The subjects in groups 2 and 3 had greater total volume and cross-sectional area in comparison to the subjects in group 1. Therefore, the bone defects receiving the electrical stimulation were demonstrated to have increased tissue growth in comparison to bone defects receiving no electrical stimulation. In addition, the subjects in groups 2 and 3 did not demonstrate significant differences from each other for total volume and cross-sectional area. Similarly, the subjects in groups 2 and 3 were further evaluated and did not show significant differences in cortical bone area fraction, average cortical thickness, trabecular number, trabecular thickness, trabecular separation, and in bone density parameters at two weeks post-operatively. Accordingly, the electrical stimulation provided by resorbable electrodes was not inferior to the electrical stimulation provided by permanent electrodes. Therefore, the resorbable electrodes are a viable option to provide electrical stimulation to induce and/or accelerate tissue growth without the downsides of permanent implanted electrodes.

Example 2

Tests were conducted to evaluate the effectiveness of therapeutic electrical stimulation provided by the resorbable implants to nerve tissue. Operations were performed on test subjects, specifically rats, to transect and repair the sciatic nerve. The sciatic nerve was transected using fine iris scissors and microsurgically repaired in a direct fashion using 10-0 nylon suture. A first group of test subjects did not receive any therapeutic electrical stimulation. A second group received therapeutic electrical stimulation using a resorbable implant. After repair and with the surgical site still open, the resorbable implant was implanted and a tissue engagement member, e.g., a cuff, was attached to the sciatic nerve of the test subjects in the second group. The controller was inserted into a subcutaneous pocked created on the dorsolateral aspect of a hind limb of each test subject. The resorbable implant and controller were secured using resorbable sutures. The surgical site was closed. The resorbable implant was wirelessly activated to deliver therapeutic electrical stimulation (monophasic, 610 200 μs pulse, 20 Hz frequency, minimum amplitude over threshold) to the sciatic nerve for 1 hour per day for 1, 3, or 6 consecutive days post-operatively.

Figure 12:
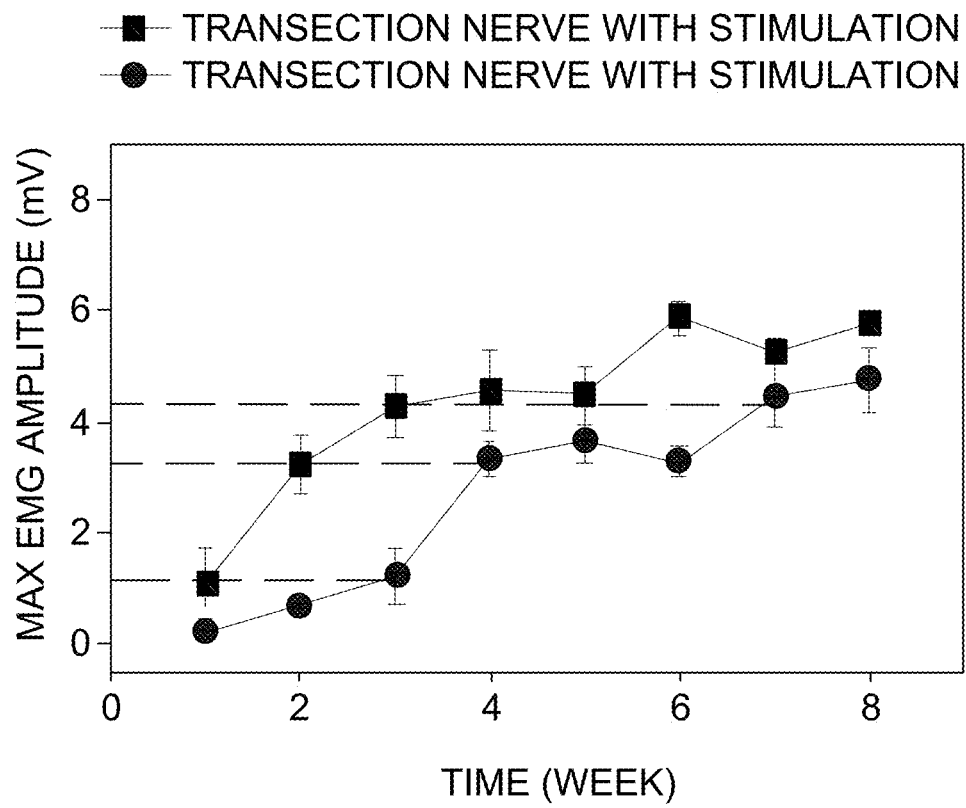
FIG. 12 is a graph comparing electromyograms measured in test subjects over an eight-week period.
Figure 13:
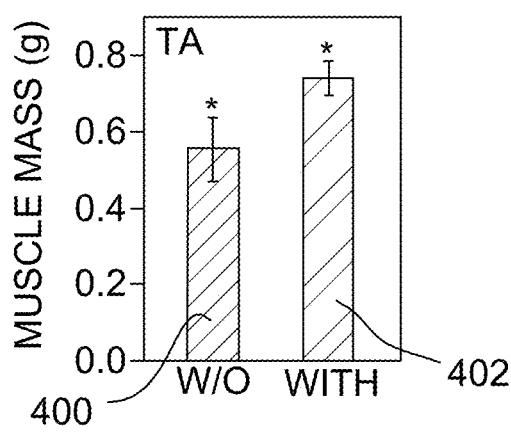
FIG. 13 is a graph comparing muscle mass measurements obtained at 8 week postoperative for the tibialis anterior (TA) muscle.
Figure 14:
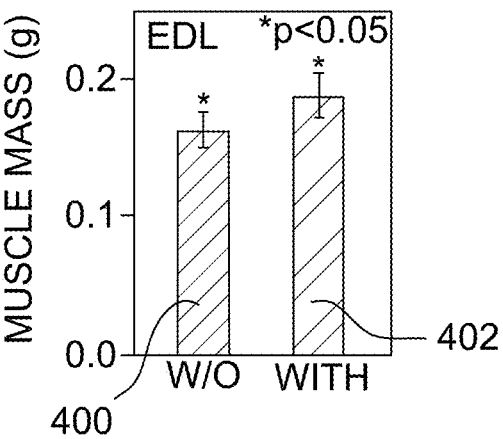
FIG. 14 is a graph comparing muscle mass measurements obtained at 8 week postoperative for the extensor digitorum longus (EDL) muscle.
Figure 15:
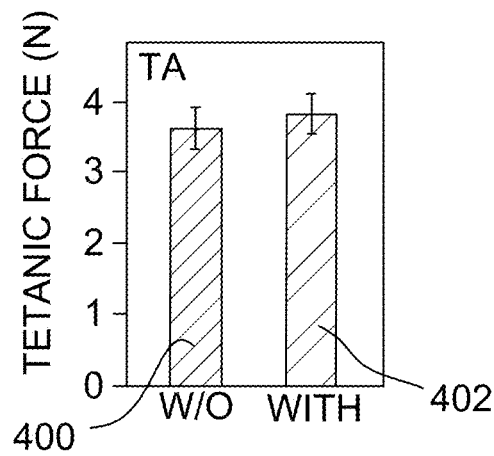
FIG. 15 is a graph comparing tetanic force measurements obtained at 8 week postoperative for the EDL muscle.
Figure 16:
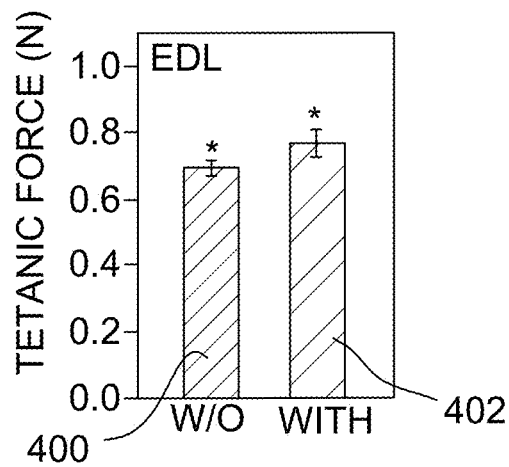
FIG. 16 is a graph comparing tetanic force measurements obtained at 8 week postoperative for the TA muscle.
Figure 17:
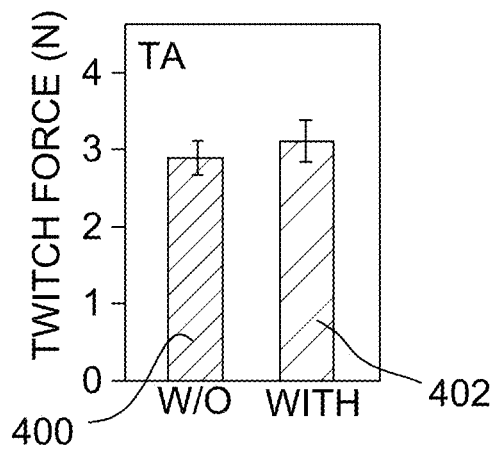
FIG. 17 is a graph comparing twitch force measurements obtained at 8 week postoperative for the EDL muscle.
Figure 18:
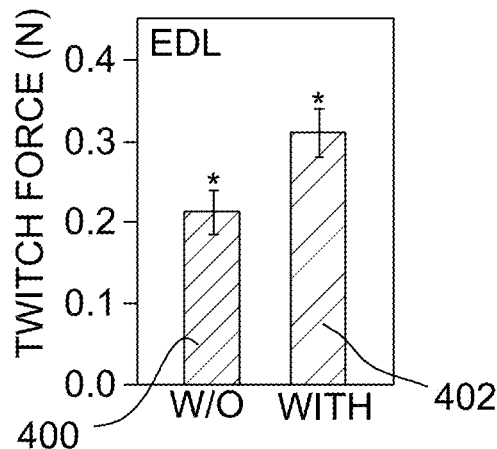
FIG. 18 is a graph comparing twitch force measurements obtained at 8 week postoperative for the TA muscle.

FIG. 12 is a graph comparing electromyograms measured in test subjects over an eight-week period. FIG. 12 includes a first curve 400 representing the first group and a second curve 402 representing the second group. The second group, which received the therapeutic electrical stimulation showed increased muscle activation. For example, muscle activation at 2 weeks post-operative for the second group is equivalent to muscle activation at 4 weeks post-operative for group 1. In addition, muscle activation at 3 weeks post-operative for the second group is equivalent to muscle activation at 7 weeks post-operative for group 1. Moreover, as seen in FIGS. 13 and 14, muscle mass measurements obtained at 8 week postoperative demonstrate that group 2 had greater muscle mass of the tibialis anterior (TA) and extensor digitorum longus (EDL) muscles following electrical stimulation than group 1. As seen in FIGS. 15-18, group 2 had increased tetanic force and twitch force in the TA and EDL muscles from electrical stimulation than group 1. Accordingly, electrical stimulation using the resorbable implant provided an increased rate of recovery for repaired transected nerves in comparison to repaired transected nerves that did not receive electrical stimulation.

Figure 19:
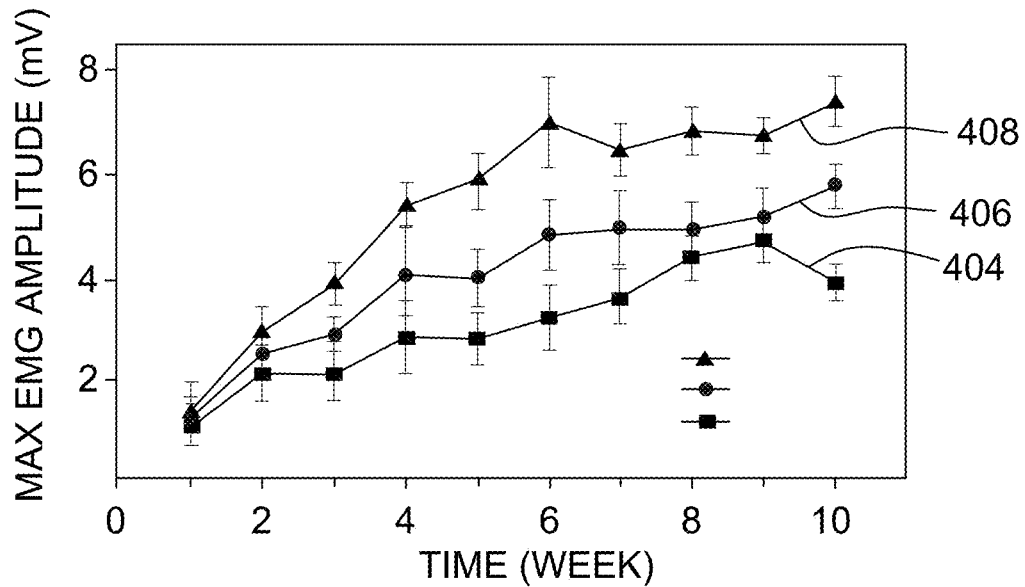
FIG. 19 is a graph comparing electromyograms measured in test subjects receiving different electrical stimulation treatments over a ten-week period.
Figure 20:
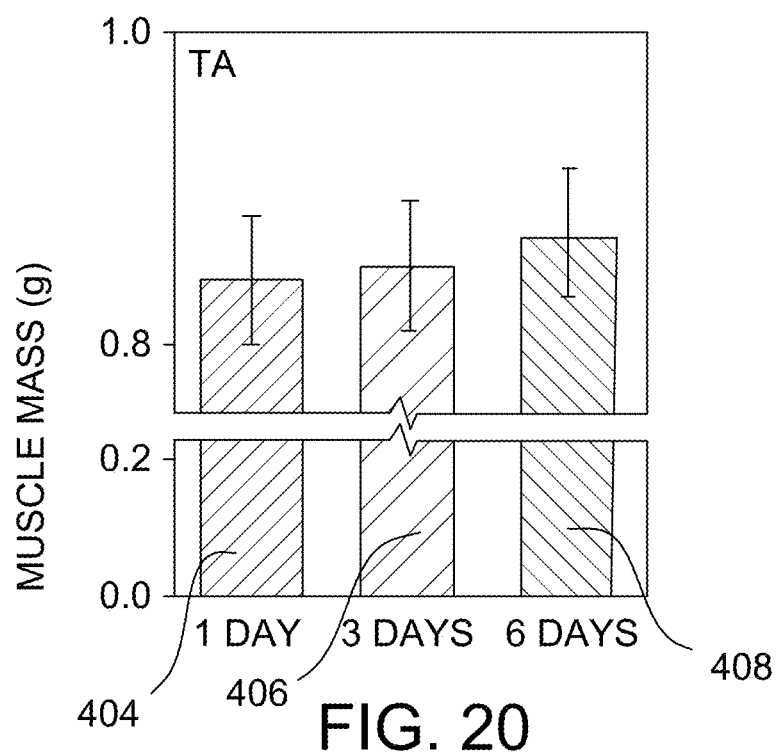
FIG. 20 is a graph comparing muscle mass measurements obtained at 10 week postoperative for the tibialis anterior (TA) muscle.
Figure 21:
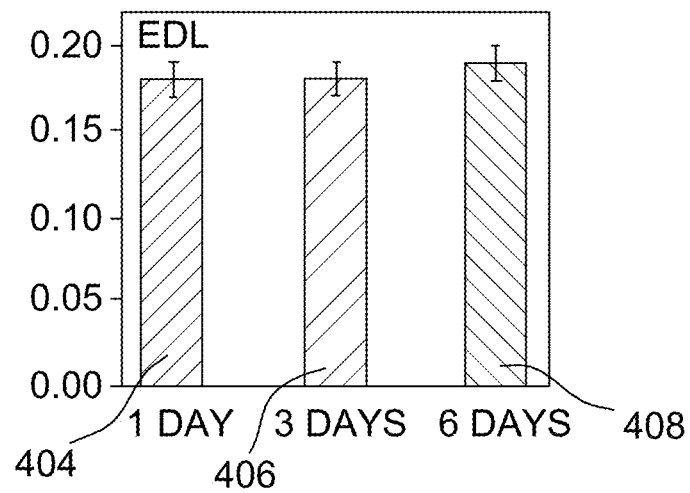
FIG. 21 is a graph comparing muscle mass measurements obtained at 10 week postoperative for the extensor digitorum longus (EDL) muscle.
Figure 22:
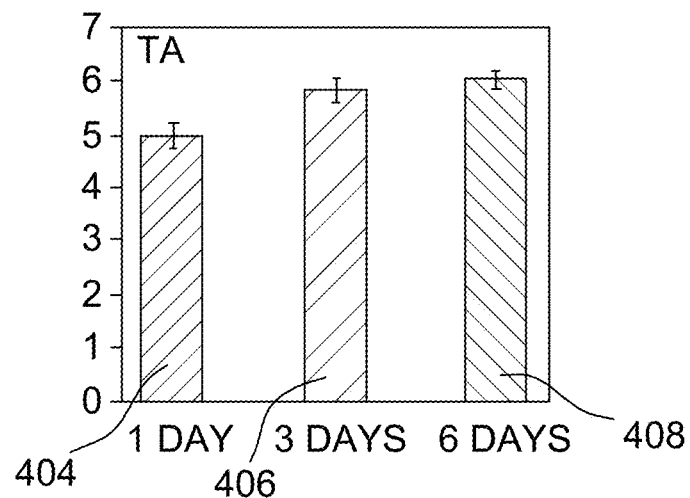
FIG. 22 is a graph comparing tetanic force measurements obtained at 10 week postoperative for the EDL muscle.
Figure 23:
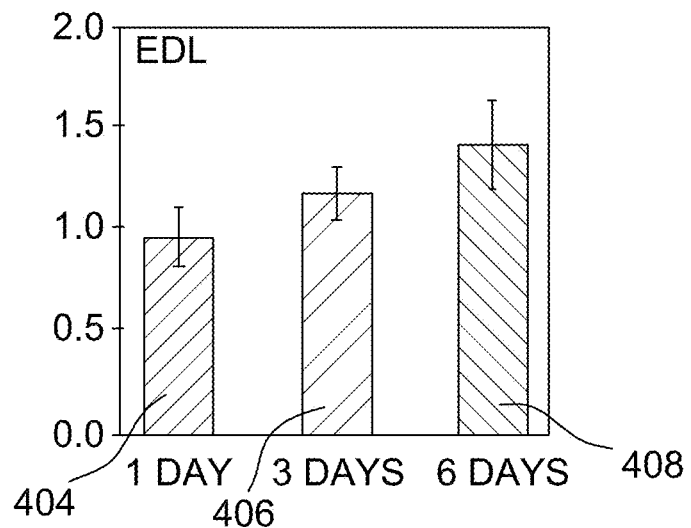
FIG. 23 is a graph comparing tetanic force measurements obtained at 10 week postoperative for the TA muscle.
Figure 24:
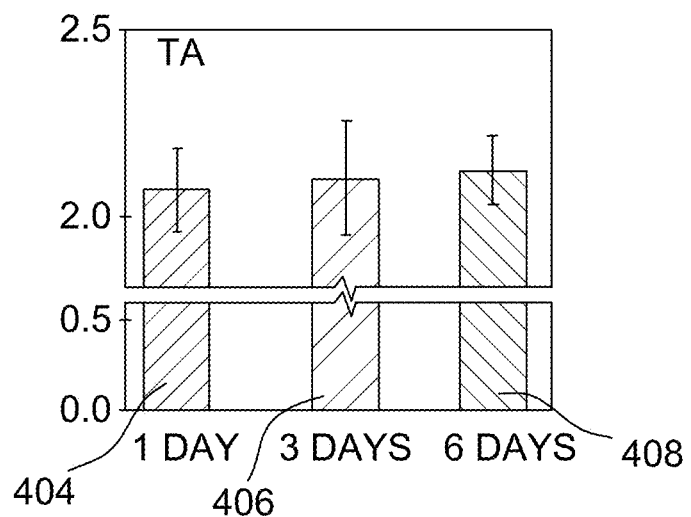
FIG. 24 is a graph comparing twitch force measurements obtained at 10 week postoperative for the EDL muscle.
Figure 25:
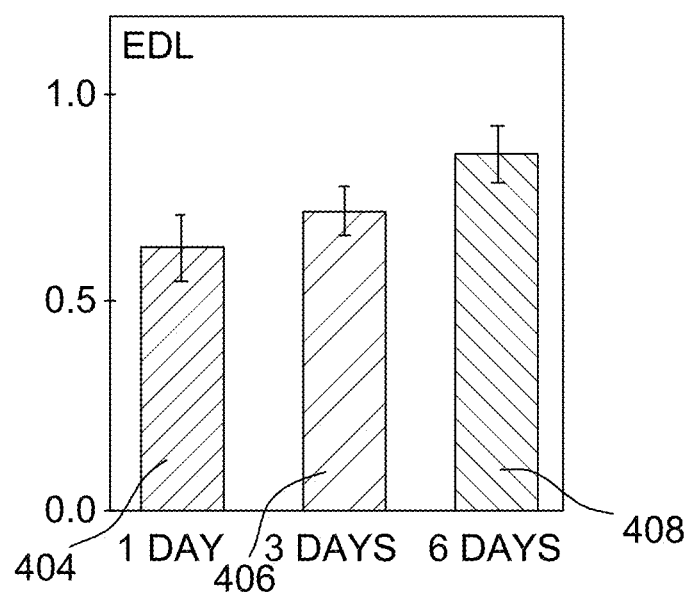
FIG. 25 is a graph comparing twitch force measurements obtained at 10 week postoperative for the TA muscle.

FIG. 19 is a graph comparing electromyograms measured in test subjects receiving different electrical stimulation treatments over a ten-week period. A first group, represented by curve 404, received electrical stimulation at the repaired sciatic nerve for 1 hour for 1 day a week. A second group, represented by curve 406, received electrical stimulation at the repaired sciatic nerve for 1 hour for 3 days a week. A third group, curve 408, received electrical stimulation at the repaired sciatic nerve for 1 hour for 6 days a week. FIGS. 20 and 21 show muscle mass measurements obtained at 8 week postoperative for the tibialis anterior (TA) and extensor digitorum longus (EDL) muscles. FIGS. 22-25 show tetanic force and twitch force in the TA and EDL muscles obtained at 8 week postoperative. Based on all measurements, the rate of recovery increased as the duration of electrical stimulation increased.

Figure 11:
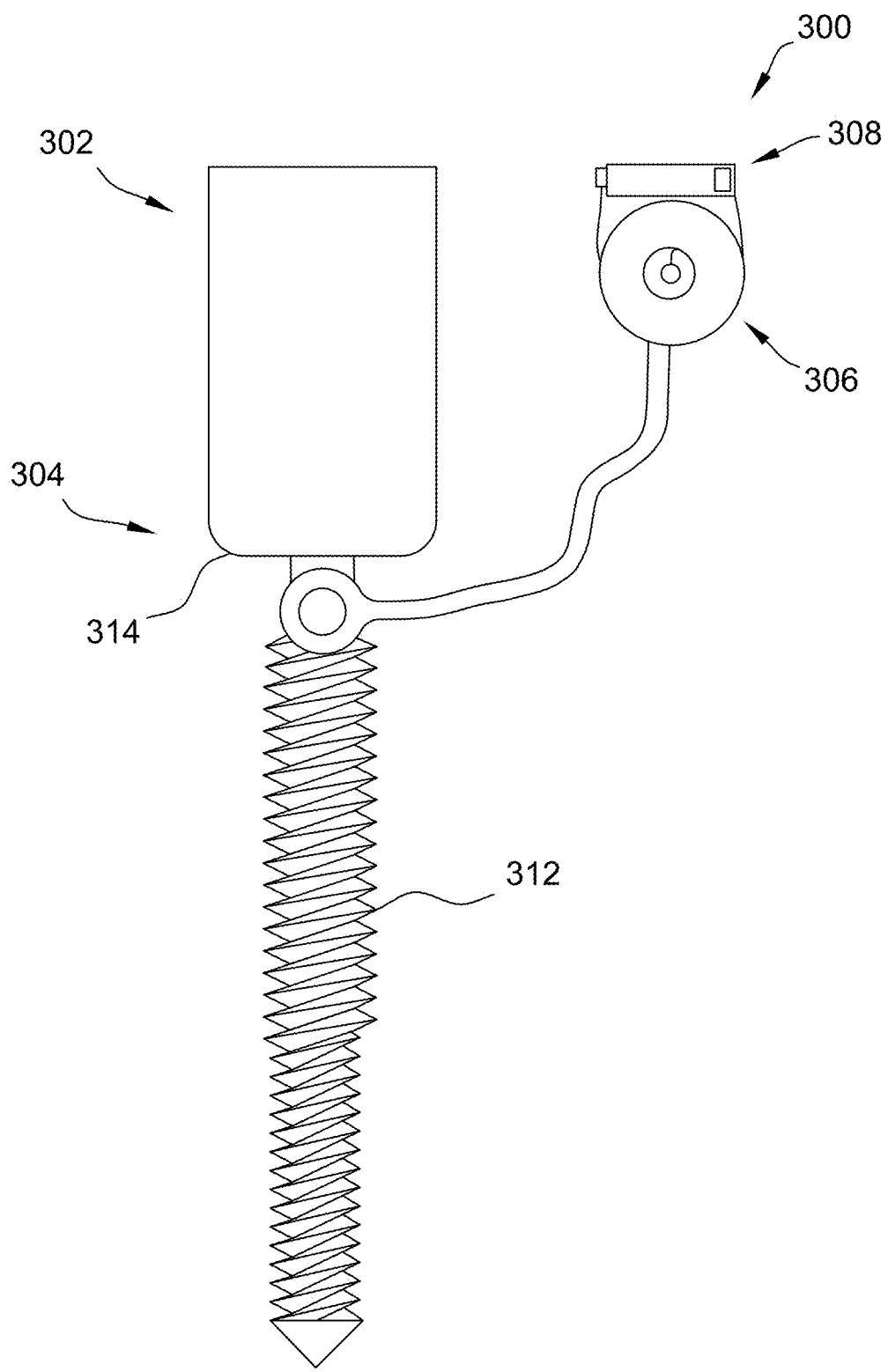
FIG. 11 is a side view of a suitable embodiment of a resorbable implant for use with the system shown in FIG. 1 including a non-resorbable component.

FIG. 11 is a side view of a suitable embodiment of a resorbable implant 300 for use with the system 10 (shown in FIG. 1). The resorbable implant 300 includes an electrode 302, a support structure 304, a transceiver 306, and electronics 308. The electronics 308 deliver electrical stimulation to a target via the electrode 302 when power is supplied to the resorbable implant 300. In addition, the electronics 308 are configured to control amplitude and duration of the electrical stimulation provided to the targeted tissue. In other embodiments, the resorbable implant 300 may include any components that enable the resorbable implant 300 to function as described herein.

In the illustrated embodiment, the support structure 304 is in the form of a bone screw and includes a threaded body 312 and a head 314. Accordingly, the support structure 304 may be attached to a bone or other body part to secure at least a portion of the resorbable implant 300 in position within the body. Specifically, the support structure 304 maintains the electrode 302 in position for the electrode 302 to electrically stimulate tissue. In the illustrated embodiment, the electrode 302 is integrated with the support structure 304. In other embodiments, the electrode 302 and the support structure 304 may be separate. Leads 310 extend from the electronics 308 to the electrode 302. In this embodiment, the support structure 304 and the electrode 302 are not resorbable. Accordingly, the support structure 304 and/or the electrode 302 may provide structural stability to the resorbable implant 300 and increase the functional life of the resorbable implant 300. In alternative embodiments, the resorbable implant 300 may include any electrode 302 and/or support structure 304 that enables the resorbable implant 300 to function as described herein.

The resorbable implant 300 includes at least some components that are fully resorbable. Specifically, the transceiver 306, the electronics 308, and the leads 310 are fully resorbable. Accordingly, the resorbable implant 300 has a reduced footprint after the service life of the resorbable implant 300. In some embodiments, portions of the resorbable implant 300 such as the electrode 302 and the support structure 304 may remain in the body as permanent implants after other components have been resorbed. In further embodiments, portions of the resorbable implant 300 such as the electrode 302 and the support structure 304 may be removed after the service life of the resorbable implant 300. In such embodiments, the resorbable implant 300 may reduce the risk of long-term complications in comparison to previous implants because the footprint of any permanent implant is reduced after resorption and/or less components are removed after the service life of the resorbable implant 300.

Embodiments of the tissue stimulation system allow electrical pulses to be applied to tissue to stimulate tissue growth and/or modify function of the tissue. For example, the systems may provide controlled pulses of DC electrical stimulation to targeted tissue treatment locations. The systems include a completely resorbable implant. Accordingly, a procedure is not required to remove the resorbable implant. In addition, the resorbable implant does not remain as a permanent implant within the body. The resorbable implant communicates wirelessly with and receives power from a controller which may be positioned exterior of the body or implanted subcutaneously. Accordingly, the resorbable implant may be positioned at tissue treatment locations that may be inaccessible by at least some previous stimulation systems.

When introducing elements of the present invention or the preferred embodiment(s) thereof, the articles "a", "an", "the", and "said" are intended to mean that there are one or more of the elements. The terms "comprising," "including", and "having" are intended to be inclusive and mean that there may be additional elements other than the listed elements.

As various changes could be made in the above constructions without departing from the scope of the invention, it is intended that all matter contained in the above description or shown in the accompanying drawings shall be interpreted as illustrative and not in a limiting sense.

What is claimed is:

1. A system for stimulating tissue, the system comprising:
    a resorbable implant including a substrate, at least one contact, electronics, and a transceiver, wherein the substrate includes a polymer sheet that is folded over to support and encapsulate the electronics and the transceiver, wherein the substrate, the at least one contact, and the transceiver are resorbable;
    a controller configured to communicate with the transceiver of the resorbable implant; and
    a power supply connected to the controller, wherein the controller delivers power to the resorbable implant from the power supply, and wherein the resorbable implant delivers electrical stimulation to the tissue when the resorbable implant receives power.

2. The system of claim 1, wherein the transceiver includes an antenna and is configured to allow the resorbable implant and the controller to communicate wirelessly.

3. The system of claim 2, wherein the resorbable implant further includes a pulse generator to deliver electric pulses to the tissue via the at least one contact when power is supplied to the resorbable implant.

4. The system of claim 2, wherein the resorbable implant further includes a power storage component to store power from the power supply.

5. The system of claim 1, wherein the resorbable implant is completely resorbable.

6. The system of claim 1, wherein the resorbable implant includes leads, two contacts, and a tissue engagement member supporting the contacts, the leads extending between the tissue engagement member and the substrate, wherein the leads are completely resorbable.

7. The system of claim 6, wherein the tissue engagement member comprises a polymer sheet.

8. The system of claim 1, wherein the resorbable implant is configured to deliver direct current (DC) electrical stimulation to the tissue.

9. The system of claim 1, wherein the at least one contact secures to nervous tissue and the resorbable implant is configured to deliver electrical pulses to the nervous tissue.

10. The system of claim 1, wherein the at least one contact secures to boney tissue and the resorbable implant is configured to deliver electrical pulses to boney tissue.

11. A method of stimulating tissue, the method comprising:
    positioning a resorbable implant at a treatment location within a body of an animal, the resorbable implant including a substrate, at least one contact, electronics, and a transceiver, wherein the substrate includes a polymer sheet that is folded over to support and encapsulate the electronics and the transceiver, wherein the substrate, the at least one contact, and the transceiver are resorbable;
    sending a signal having a frequency in a range of 1 Megahertz (MHz) to 10 MHz to the transceiver from a controller positioned on an exterior of the body, wherein the transceiver is supported by the substrate;
    receiving power at the resorbable implant from a power supply connected to the controller; and
    providing electrical stimulation to the tissue at the treatment location through the at least one contact.

12. The method of claim 11, wherein providing electrical stimulation to the tissue at the treatment location comprises providing DC electrical stimulation to boney tissue at the treatment location.

13. The method of claim 11, further comprising positioning a tissue engagement member of the resorbable implant on nervous tissue at the treatment location, wherein providing the electrical stimulation comprises providing the electrical stimulation to the nervous tissue.

14. A resorbable implant for providing electrical pulses to stimulate tissue, the resorbable implant comprising:
    a transceiver configured to receive signals from a controller;
    electronics configured to provide electrical pulses based on the signals received from the controller;
    a substrate supporting the transceiver and the electronics;

contacts configured to be positioned on the tissue to deliver the electrical pulses to the tissue; and leads extending between the substrate and the contacts, wherein the contacts, substrate, electronics, leads, and transceiver are completely resorbable.

15. The resorbable implant of claim 14 further comprising a tissue engagement member supporting the contacts to secure the contacts on the tissue.

16. The resorbable implant of claim 14, wherein the transceiver includes a coil antenna.

17. The resorbable implant of claim 14, wherein the substrate comprises a polymer sheet that is folded over to support and encapsulate the electronics and the transceiver.

18. The resorbable implant of claim 14, wherein the resorbable implant receives power from the controller and is configured to deliver DC current to the tissue when the resorbable implant receives power from the controller.

19. The resorbable implant of claim 18, further comprising a power storage component configured to store power received from the controller.

\* \* \* \* \*